United States Patent [19]
O'Connor

[11] Patent Number: 6,162,959
[45] Date of Patent: Dec. 19, 2000

[54] FOLDED FLUID ABSORBING STRIP

[75] Inventor: Lawrence J. O'Connor, Winnipeg, Canada

[73] Assignee: KT Industries Inc., Wayne, Ind.

[21] Appl. No.: 09/158,824

[22] Filed: Sep. 23, 1998

[51] Int. Cl.$^7$ .................................................. A61F 13/00
[52] U.S. Cl. .............................. 602/41; 602/42; 602/43; 602/44; 602/45; 602/46
[58] Field of Search .......................... 602/41, 58, 42–46; 128/888; 604/304, 307

[56] References Cited

U.S. PATENT DOCUMENTS

| | | |
|---|---|---|
| 4,560,379 | 12/1985 | Stemmler . |
| 4,650,480 | 3/1987 | Stemmler . |
| 5,246,770 | 9/1993 | Bottiglione et al. . |
| 5,465,735 | 11/1995 | Patel . |
| 5,593,395 | 1/1997 | Martz . |

FOREIGN PATENT DOCUMENTS

| | | |
|---|---|---|
| 0 649 644 A1 | 4/1995 | European Pat. Off. . |
| 0 829 245 A2 | 3/1998 | European Pat. Off. . |
| WO95/03019 | 2/1995 | WIPO . |

*Primary Examiner*—Michael A. Brown
*Assistant Examiner*—Lalita M. Hamilton
*Attorney, Agent, or Firm*—Adrian D. Battison

[57] ABSTRACT

A fluid absorbent tape is formed from a fluid permeable strip which is folded to form overlapping portions enclosing an area filled with a band of a fluid absorbent particulate material lying on at least a part of a width of the upper surface of the strip. In one example, the strip is folded along one longitudinally extending fold line centrally between the side edges of the strip such that the side edges overlie on another and are bonded together by a bead of hot melt adhesive, a strip of EAA or other suitable method. In another arrangement, the side edges are folded together to form a butt joint which is bonded by an overlying or underlying strip of EAA or similar material. A second band of material can be provided in a second folded portion overlying the first to form an S-shape with both being maintained encapsulated by the bonding of the side edges of the strip.

12 Claims, 3 Drawing Sheets

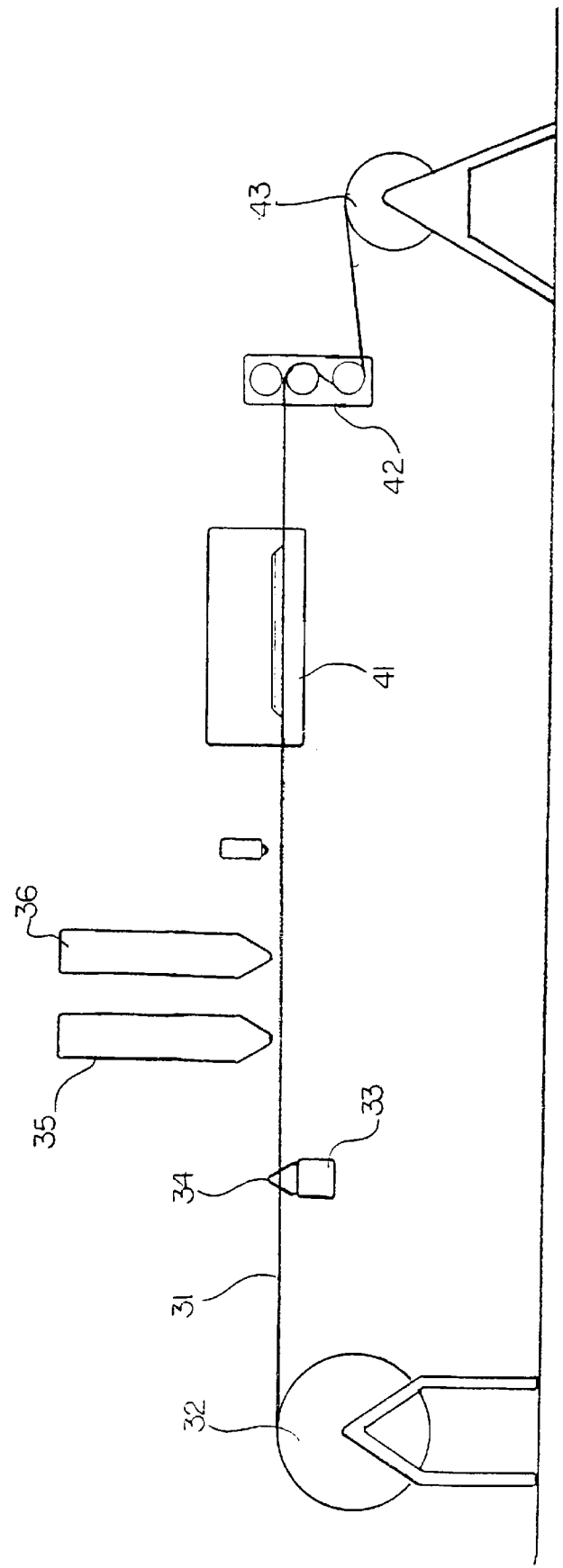

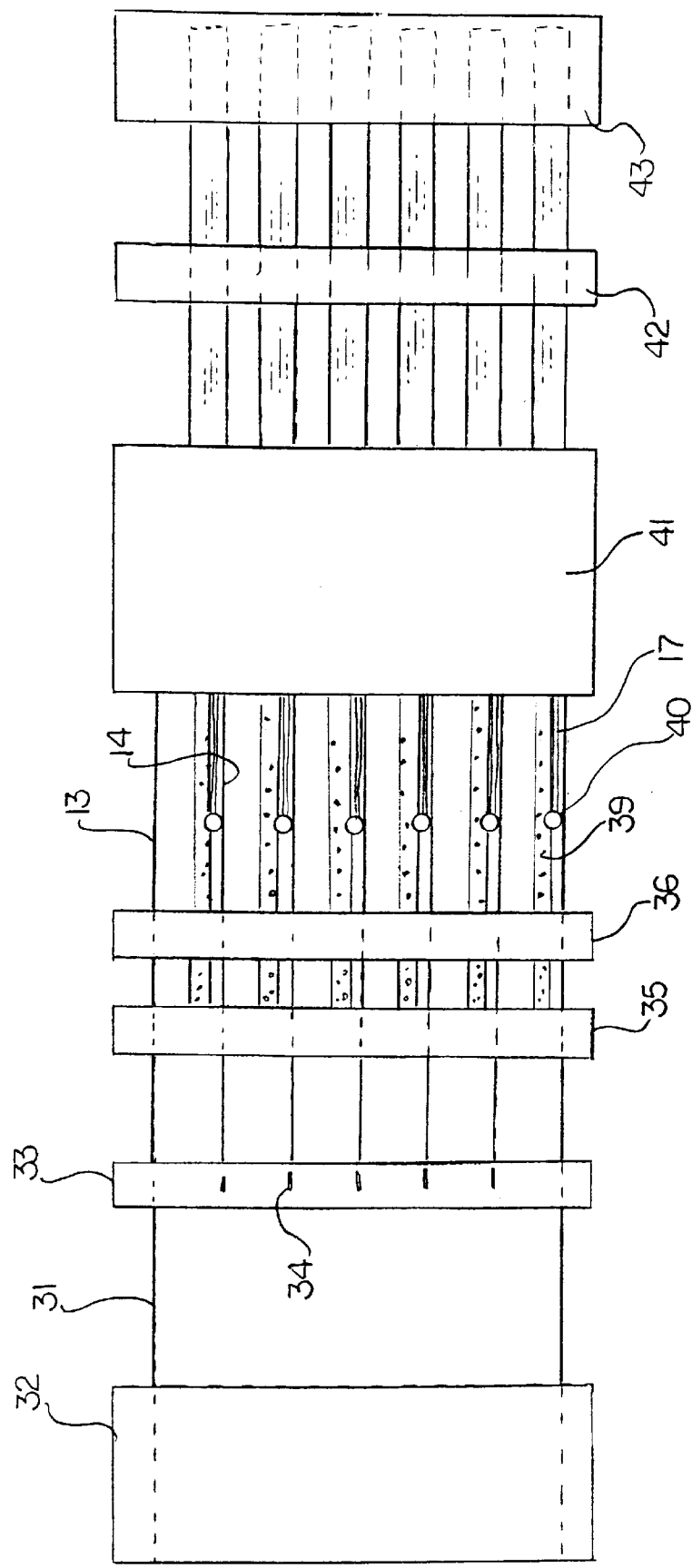

FOLDED FLUID ABSORBING STRIP

This invention relates to a package of a continuous strip of material of a type formed by a supporting structure including at least two overlying fibrous layers containing between the layers of the supporting structure a loose material particulate material of the type for absorbing fluid.

BACKGROUND OF THE INVENTION

Strips of material of this type are used for manufacture of diapers and other absorbent products such as feminine napkins. The strip generally contains a particulate material of the type known as a Super Absorbent Polymer for use in absorbing and containing moisture. Additional particulate materials can also be included for example deodorants, baking soda and zeolite.

The strips are generally cut from a wider web of the above material so that each strip has a tendency to release the powder at the side edges which are cut from the wider web. Recent developments in this field have lead to thicker and more complex materials with an increased tendency to release powder on the manufacturing line. This is disadvantageous since it leads to loss of the valuable powder and more importantly the release of the powder into the atmosphere leads to an unacceptable manufacturing environment.

Commercially in the field, tapes have been manufactured of the type known as C-fold in which a strip is folded along two space fold lines to form a flat base onto which the particulate material is applied to be carried thereby and two overlying leaves each extending from a respective fold line, the leaves overlapping in the middle of the base so as to contain the particulate material. This tape is often formed on line with the assembly machinery. However the on line formation of the tape is becoming unacceptable due to the release of the powder on the line and due to the increase in speed which has become available with recently developed assembly machinery. The trend in this industry is therefore for the manufacturer of the end product to become merely an assembler of the various components with those components being supplied by other specialist manufacturers.

In PCT Patent application Publication WO95/03019 of Korma SRL published on Feb. $2^{nd}$ 1995 is disclosed a method of manufacturing a strip of this type which uses a fluid absorbing powder in admixture with a heat actuable adhesive powder. The powders are retained between two layers which are of a fluid permeable material such as paper which allows penetration of the fluid to the powder. In addition to the above powders, there are added lines of adhesive between the layers which act to bond the layers together to form a web. The adhesive lines allow slitting of the web into separate strips at the adhesive lines to form strips which have the edges sealed by the adhesive. This arrangement has achieved some commercial success and is becoming accepted as a preferred construction for supplying the absorbent powder. However the construction requires additional material in the layers in view of the width of the adhesive lines which reduce the actual working width of the strip that is the area containing the powder.

In an alternative field, that is the use of water absorption tapes to block migration of moisture through cables such as fiber-optic cables, there is provided a further teaching concerning a technique for manufacture of a suitable strip or tape of this type. Thus in U.S. Pat. No. 5,246,770 (Bottiglione) assigned to Intissel SA and published Sept. $21^{st}$ 1993 is disclosed a method of manufacturing a strip of this type which uses a water swellable powder in admixture with a heat actuable adhesive powder. The powders are retained between two layers one of which is dissolvable in water to allow access of the water to the powder. The heat actuable powder is used to seal the layers together to hold the powder in place. This technique using air laid paper for the layers was also in public use around the same time.

SUMMARY OF THE INVENTION

It is one object of the present invention, therefore, to provide an improved method for manufacturing a fluid absorbent strip and to provide an improved tape.

According to one aspect of the invention there is provided a method of supplying a fluid absorbent strip comprising:

providing a web of a fluid permeable sheet material;

longitudinally slitting the web into a plurality of strips of the sheet material, each strip having an upper surface and two side edges;

applying longitudinally along the strip a fluid absorbent particulate material onto at least a part of a width of the upper surface of the strip to define a band of the particulate material;

folding the strip along at least one longitudinally extending fold line arranged between the side edges of the strip such that a part of the width of the strip is folded over to cover the band and such that at least one of the edges of the strip lies adjacent to or in contact with a longitudinally extending part of the strip;

and bonding said at least one of the side edges of the strip to said longitudinally extending part of the strip to encapsulate the band of particulate material.

Preferably wherein the side edge is bonded by an adhesive strip which may be an hot melt adhesive.

Preferably the strip is folded substantially along a center line of the strip such that said one edge overlies the other edge and wherein the edges are bonded together.

Preferably the edges are bonded together by a bead of an adhesive material extending along and between the edges.

Preferably a second strip of an adhesive material is applied along the fold line to form a bonded strip at the fold line.

Preferably both side edges are folded along respective fold lines spaced outwardly from the center line of the strip such that the side edges are brought together at a position overlying the band where the side edges are bonded together.

Preferably the side edges are brought to a butt joint.

Preferably the butting side edges are bonded by an adhesive strip overlying the butting side edges and external of the encapsulated band.

Preferably the butting side edges are bonded by an adhesive strip underlying the butting side edges and in between the side edges and the encapsulated band.

Preferably the adhesive strip is slit from a web of an adhesive sheet.

Preferably the method further includes:

applying longitudinally along the strip a second particulate material onto at least a second part of a width of the strip to define a second band of the second particulate material;

folding the strip along a second longitudinally extending fold line arranged between the side edges of the strip such that a part of the width of the strip is folded over to cover the second band and such that the other of the edges of the strip lies adjacent to or in contact with a longitudinally extending part of the strip;

and bonding said other of the side edges of the strip to said longitudinally extending part of the strip to encapsulate the second band of particulate material.

Preferably the strip is folded such that the first band overlies the second band on the other side of the strip such that the first and second bands are separated by the strip.

Preferably the strip is folded into an S-shape with the first band on one side and the second band on the other side.

According to a second aspect of the invention there is provided a fluid absorbent tape comprising:

a fluid permeable strip having an upper surface and two side edges;

a band of a fluid absorbent particulate material lying on at least a part of a width of the upper surface of the strip;

the strip being folded along at least one longitudinally extending fold line arranged between the side edges of the strip such that a part of the width of the strip is folded over to cover the band and such that at least one of the edges of the strip lies adjacent to or in contact with a longitudinally extending part of the strip;

said at least one of the side edges of the strip being bonded to said longitudinally extending part of the strip to encapsulate the band.

BRIEF DESCRIPTION OF THE DRAWINGS

One embodiment of the invention will now be described in conjunction with the accompanying drawings in which:

FIGS. 6 and 7 together are a schematic illustration of a method for forming the strips of FIGS. 1 to 5, FIG. 6 being a side elevational view and FIG. 7 being a top plan view.

In the drawings like characters of reference indicate corresponding parts in the different figures.

DETAILED DESCRIPTION

Figure 1:
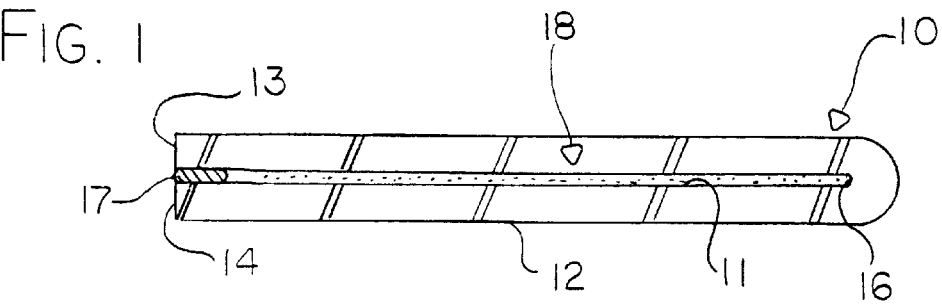
FIG. 1 is a schematic cross-sectional view of a first embodiment of strip according to the present invention.

In FIGS. 1 through 4 are shown four examples of a fluid absorbent tape. Each tape is formed from a strip of a fluid permeable material such as air-laid paper. The strip is initially slit from a wider web of the material so that the strip is wholly formed from a common material defining the web. The strip is indicated in each figure at 10 and has an upper surface 11, a bottom surface 12, a first side edge 13 and a second side edge 14.

In each embodiment the strip is generally folded about a longitudinal fold line so that the side edges are brought together to encapsulate a hollow interior 15 of the strip. Within the hollow interior is encapsulated a particulate material which contains a fluid absorbent particulate material such as super absorbent polymer as well as a heat activatable bonding powder.

Examples of the above particulate materials are well known to one skilled in the art from the commercial products presently available and from the above mentioned patents.

In addition to the fluid absorbent particulate material, there may be also contained within the strip other particulate materials such as baking soda, deodorants and zeolite which is a material of a character which absorbs ammonia.

In the embodiment of FIG. 1, the strip is folded at a fold line 16 so that two halves of the strip are laid one on top of the other bringing the side edges 13 and 14 together with the side edge 13 overlying the side edge 14. The two halves of the strip are bonded together by a bead 17 of an adhesive material which Is preferably a hot melt adhesive applied as a bead along the edge 14 onto which the edge 13 is compressed. The bead is of minimum width sufficient to achieve the bonding effect leaving the remainder of the strip free from the adhesive bead. Thus the fold line 16 is free from adhesive and the whole of the strip apart from the area adjacent the bead 17 is available for penetration by fluid for that fluid to access the powder indicated schematically at 18 within the hollow interior 15.

Figure 2:
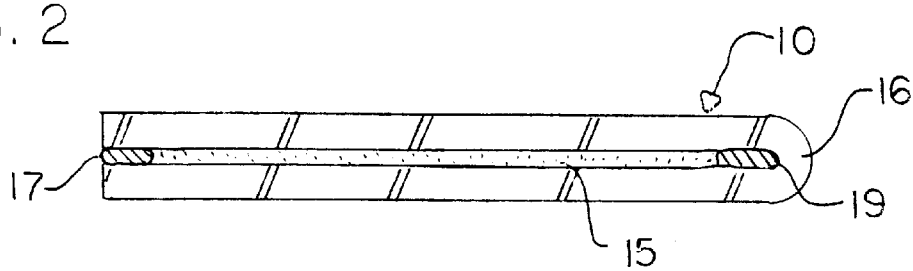
FIG. 2 is a schematic cross-sectional view of a second embodiment of strip according to the present invention.

In FIG. 2 is shown a tape substantially of the same construction as that shown in FIG. 1 except that in addition there is provided a second bead 19 of adhesive which is substantially the same as the bead 17 but is arranged at the fold line 16. Thus in this embodiment the tape is substantially symmetrical in that each side of the tape is formed by overlying portions of the strip bonded together by the respective bead 17, 19.

This arrangement has the advantage that the strip is symmetrical so that it should perform symmetrically and remain symmetrical when moisture engages the strip in use.

The tape of FIG. 1 may in some examples tend to provide more absorption of moisture at the fold line 16 than at the bead 17 leading to some tendency of the tape to expand more in that area, which may detract from the appearance of the product in use.

However the embodiment of FIG. 1 has the advantage over the embodiment of FIG. 2 that the area of the strip which is available for absorption of moisture is of increased width since there is no second bead which would otherwise interfere with the absorption of moisture in that area.

Figure 3:
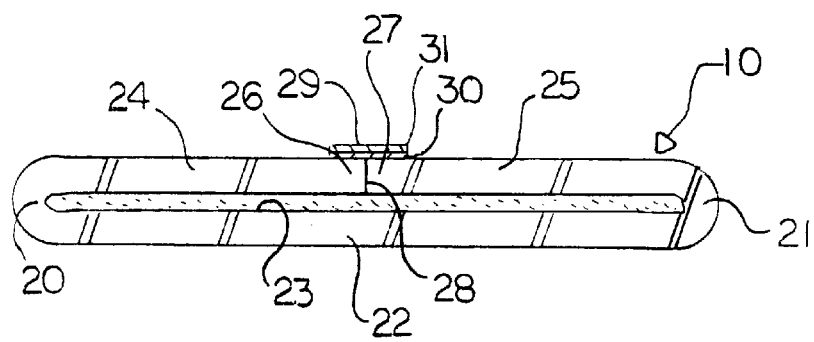
FIG. 3 is a schematic cross-sectional view of a third embodiment of strip according to the present invention.
Figure 4:
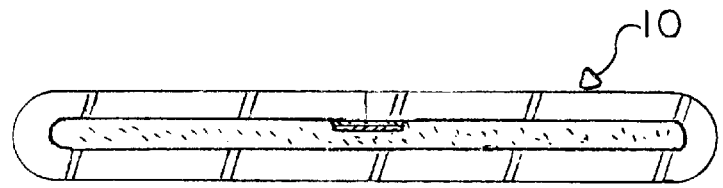
FIG. 4 is a schematic cross-sectional view of a fourth embodiment of strip according to the present invention.

Turning now to FIGS. 3 and 4, there is shown a similar construction formed from the strip 10 but in these embodiments the strip is folded at two separate fold lines 20 and 21 to form a base portion 22 of the strip having an upper surface 23 on which the particulate material is applied. The fold lines 20 and 21 thus define folded leaves 24 and 25 of the strip which are brought together so that the side edges 26 and 27 meet at a butting center line 28 to form a butt joint.

The side edges 26 and 27 are bonded together at the butt joint by a strip 29 of an adhesive material. The strip 29 is preferably formed from a layer 30 of an adhesive material such as EAA carried on a support strip 31 of a suitable carrier material. The strip 29 is slit form a web of the two layers 30 and 31 so as to form a narrow strip of the required width simply to bond the butting side edges together.

In the embodiment shown in FIG. 4, the construction is substantially identical except that the layer 29 is applied on the inside surface of the butting side edges 26 and 27 rather than on the outside surface as shown in FIG. 3.

The tape is used in practice in the embodiments in FIG. 3 and 4 using the base layer 22 as the absorbent layer facing the source of moisture to be absorbed. Thus the other layer defined by the leaves 24 and 25 forms a rear layer away from the source to reduce the possibility of the strip 29 from interfering with the absorbency of the tape.

In each embodiment, therefore, the powders forming the particulate material 18 are applied in a band on the base portion of the strip before the top portion or portions of the strip are folded over to cover the band and encapsulate the band.

The embodiments of FIG. 3 and 4 have the significant advantage that the tape is symmetrical but that the whole of the width of the tape from the fold lines 20 and 21 across the base layer 22 provides a complete absorption area which is not restricted by any areas of adhesive. Thus the full width of the tape is an operating width and there are no wasted portions of the tape on either side of the tape which are provided simply for bonding of the adhesive strips or adhesive beads. In order to provide an operating width of the tape therefore, as much as 25% of the material cost is reduced by reducing the wasted areas at the adhesive beads.

Figure 5:
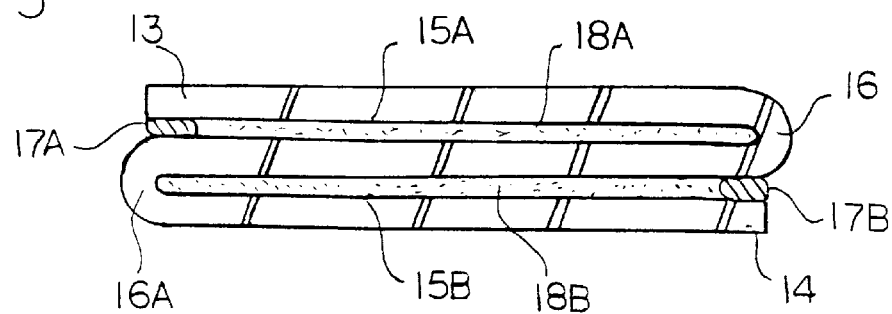
FIG. 5 is a schematic cross-sectional view of a fifth embodiment of strip according to the present invention.

In the embodiment of FIG. 5, the strip of FIG. 1 is modified to include two fold lines 16 and 16A thus forming two separate overlying areas 15 and 15A. The strip is folded into an S-shape in that the a first bead line 17A bonds the side edge 13 to an intermediate part of the strip, in that the fold line 16A acts to turn a second part of the strip back under the first part and in that the second bead 17B of adhesive acts to bond the side edge 14 under an second intermediate part of the strip. Thus the two bands 18A and 18B are arranged directly overlying and can contain two particulate materials of different character which are preferably maintained separate. In an alternative folding arrangement, the fold line 16A is turned up (not shown) so as to wrap outside the bead 17A and so that the area 15B is on top of the area 15A. In addition, yet further areas can be formed for containing further bands of material by providing yet further fold lines. This arrangement therefore allows additional material to be carried into the finished assembled product using a single strip for carrying the different materials.

In FIGS. 6 and 7 is shown schematically a method for forming the tape of FIG. 1. Thus a web 31 is supplied from a suitable supply schematically indicated at 32 and passes over a slitting bar 33 including a plurality of slitting knives 34 which slit the web into a plurality of parallel side by side strips 10. Particulate material forming the bonding agent is provided in a supply indicated at 35 and particulate material forming the super absorbent polymer is provided in supply indicated at 36. These materials are mixed in a mixing chamber schematically indicated at 37 for supply to a dispenser 38. The dispenser is arranged to lay down onto one part of the strip 10 a band 39 of the mixed powder. The band has a width equal to one half of the width of the strip 10 and is arranged adjacent the side edge 14 of the strip. The bead 17 is laid down on the strip adjacent the side edge 14 from an adhesive applicator 40. A folding shoe 41 acts to fold the strip portion which is free from the band 39 so that strip portion and the associated side edge 13 is folded over onto the side edge 14 and onto the bead 17.

When folded, the strip is passed through a nip of a pair of heated calendar rolls 41 which apply pressure onto the folded strip so as to crease the fold line 16 and to complete the adhesive connection of the side edges 13 and 14 by activating or pressurising the bead 17. Simultaneously the calendar rolls act to apply sufficient heat to activate the bonding agent from the supply 35 so that the layers of the strip are bonded to the powder thus encapsulating and enclosing the SAP powder in the band 39.

A suitable mixing chamber 37, dispensing chamber 38, adhesive applicator 40, folding shoe 41 and calendar rolls 42 are well known to one skilled in the art so that the various elements of the method can be put together to provide the operation and method as set forth above.

The method for forming the tape of FIG. 2 involves merely the addition of a second adhesive applicator 40 along the centre line of the strip 10.

The methods for forming the tapes of FIGS. 3, 4 and 5 involve minor modification including the use of two folding shoes which act to fold both side edges inwardly and define the fold lines 20 and 21. A tape supply for supplying the strip 29 can be added and is well known to one skilled in the art. Two dispensing systems for the two bands can be provided at the required location in the line In an alternative arrangement (not shown) the bead of adhesive shown at 17, 17A or 17B can be replaced by an alternative form of bonding. This can include a strip of EAA as shown in FIGS. 3 and 4 or can include heat sealing or welding where the properties of the strip allow or can include mechanical bonding such as by crimping or needling.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

What is claimed is:

1. A method of supplying a fluid absorbent strip comprising:

providing a web of a fluid permeable sheet material;

longitudinally slitting the web into a plurality of strips of the sheet material, each strip having an upper surface and two side edges;

applying longitudinally along the strip a fluid absorbent particulate material onto at least a part of a width of the upper surface of the strip to define a band of the particulate material;

folding the strip along two parallel, longitudinally extending fold lines arranged between the side edges of the strip and spaced outwardly from the center line of the strip such that the side edges are brought together at a position overlying the band to cover the band;

and bonding together said brought together side edges of the strip by an adhesive strip overlying the side edges and external of the band to encapsulate the band of particulate material.

2. The method according to claim 1 wherein the side edges are brought to a butt joint.

3. The method according to claim 1 wherein the adhesive strip is slit from a web of an adhesive sheet.

4. A fluid absorbent tape comprising:

a fluid permeable strip having an upper surface and two side edges;

a band of a fluid absorbent particulate material lying on at least a part of a width of the upper surface of the strip;

the strip being folded along two parallel, longitudinally extending fold lines arranged between the side edges of the strip and spaced outwardly from the center line of the strip such that the side edges are brought together at a position overlying the band to cover the band;

said brought together side edges of the strip being bonded together by an adhesive strip overlying the side edges and external of the band to encapsulate the band.

5. The tape according to claim 4 wherein the side edges are arranged to define a butt joint therebetween.

6. The tape according to claim 4 wherein the adhesive strip is slit from a web of an adhesive sheet.

7. A method of supplying a fluid absorbent strip comprising:

providing a web of a fluid permeable sheet material;

longitudinally slitting the web into a plurality of strips of the sheet material, each strip having an upper surface and two side edges;

applying longitudinally along the strip a fluid absorbent particulate material onto at least a part of a width of the upper surface of the strip to define a band of the particulate material;

folding the strip along two parallel, longitudinally extending fold lines arranged between the side edges of the strip and spaced outwardly from the center line of the strip such that the side edges are brought together at a position overlying the band;

and bonding together said brought together side edges of the strip by an adhesive strip underlying the side edges and in between the side edges and the band to encapsulate the band of particulate material.

8. The method according to claim 7 wherein the side edges are brought to a butt joint.

9. The method according to claim 7 wherein the adhesive strip is slit from a web of an adhesive sheet.

10. A fluid absorbent tape comprising:

a fluid permeable strip having an upper surface and two side edges;

a band of a fluid absorbent particulate material lying on at least a part of a width of the upper surface of the strip;

the strip being folded along two parallel, longitudinally extending fold lines arranged between the side edges of the strip and spaced outwardly from the center line of the strip such that the side edges are brought together at a position overlying the band to cover the band;

said brought together side edges of the strip being bonded together by an adhesive strip underlying the side edges and in between the side edges and the band to encapsulate the band.

11. The tape according to claim 10 wherein the side edges are arranged to define a butt joint therebetween.

12. The tape according to claim 10 wherein the adhesive strip is slit from a web of an adhesive sheet.

* * * * *